United States Patent
Yi et al.

(10) Patent No.: US 11,046,828 B2
(45) Date of Patent: Jun. 29, 2021

(54) FABRICATION OF MACROPOROUS MONODISPERSE HYDROGEL MICROSPHERES

(71) Applicant: Trustees of Tufts College, Medford, MA (US)

(72) Inventors: Hyunmin Yi, Lexington, MA (US); Sukwon Jung, Incheon (KR)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 15/568,267

(22) PCT Filed: Apr. 20, 2016

(86) PCT No.: PCT/US2016/028344
§ 371 (c)(1),
(2) Date: Oct. 20, 2017

(87) PCT Pub. No.: WO2016/172143
PCT Pub. Date: Oct. 27, 2016

(65) Prior Publication Data
US 2018/0105666 A1    Apr. 19, 2018

Related U.S. Application Data

(60) Provisional application No. 62/150,626, filed on Apr. 21, 2015.

(51) Int. Cl.
| | |
|---|---|
| *C08J 9/00* | (2006.01) |
| *A61K 47/69* | (2017.01) |
| *C08J 3/075* | (2006.01) |
| *C08J 3/24* | (2006.01) |
| *B29C 67/20* | (2006.01) |
| *C08L 5/08* | (2006.01) |
| *A61K 9/16* | (2006.01) |
| *B29C 35/08* | (2006.01) |
| *B29K 71/00* | (2006.01) |
| *B29K 105/00* | (2006.01) |

(52) U.S. Cl.
CPC ........... *C08J 9/0061* (2013.01); *A61K 9/1652* (2013.01); *A61K 47/6925* (2017.08); *B29C 67/20* (2013.01); *C08J 3/075* (2013.01); *C08J 3/246* (2013.01); *C08L 5/08* (2013.01); *B29C 35/0805* (2013.01); *B29C 2035/0827* (2013.01); *B29K 2071/02* (2013.01); *B29K 2105/0061* (2013.01); *C08J 2205/022* (2013.01); *C08J 2207/10* (2013.01); *C08J 2371/02* (2013.01); *C08J 2405/08* (2013.01)

(58) Field of Classification Search
None
See application file for complete search history.

(56) References Cited

U.S. PATENT DOCUMENTS

| | | | | |
|---|---|---|---|---|
| 2005/0143484 | A1* | 6/2005 | Fang | C08G 65/329 523/122 |
| 2006/0239960 | A1* | 10/2006 | Bossard | C12N 9/52 424/78.27 |
| 2010/0113708 | A1* | 5/2010 | Hartmann | C08G 85/004 525/374 |
| 2010/0291055 | A1* | 11/2010 | Athanasiadis | A61L 26/0052 424/94.1 |
| 2012/0196770 | A1* | 8/2012 | Agresti | C12Q 1/02 506/12 |
| 2012/0308508 | A1* | 12/2012 | Saunders | A61L 27/00 424/78.18 |
| 2014/0370500 | A1* | 12/2014 | Ghanavi | A61K 9/5123 435/6.1 |

OTHER PUBLICATIONS

Bhattarai et al "PEG-Grafted Chitosan as an Injectable Thermosensitive Hydrogel for Sustained Protein Release" Journal of Controlled Release vol. 103, pp. 609-624, 2005.
Buranachai et al "Chitosan/Polyethylene Glycol Beads Crosslinked with Tripolyphosphate and Glutaraldehyde for Gastrointestinal Drug Delivery" AAPS PharmSciTech vol. 11, pp. 1128-1137, 2010.
Jung et al "Facile Micromolding-Based Fabrication of Biopolymeric-Synthetic Hydrogel Microspheres with Controlled Structures for Improved Protein Conjugation" Chemistry of Materials vol. 27, pp. 3988-3998, 2015.
Prego et al "Chitosan-PEG Nanocapsules as New Carriers for Oral Peptide Delivery Effect of Chitosan Pegylation Degree" Journal of Controlled Release vol. 111, pp. 299-308, 2006.
Selvam et al "Swellable Hydrogel Particles for Controlled Release Pulmonary Administration Using Propellant-Driven Metered Dose Inhalers" Journal of Aerosol Medicine and Pulmonary Drug Delivery vol. 24, pp. 25-34, 2011.
Yeh et al "Micromolding of Shape-Controlled, Harvestable Cell-Laden Hydrogels" Biomaterials vol. 27, pp. 5391-5398, 2006.
International Search Report and Written Opinion for International Application No. PCT/US2016/028344 dated Jun. 29, 2016.

* cited by examiner

*Primary Examiner* — Ronak C Patel
(74) *Attorney, Agent, or Firm* — Dana M. Gordon; Foley Hoag LLP

(57) ABSTRACT

A macroporous polymeric hydrogel microsphere that contains poly(ethylene glycol), chitosan, and water. The hydrogel microsphere, having a diameter of 50-250 µm and a mesh size of 5-100 nm, is capable of transporting biomolecules conjugated to it. Also disclosed is a method of fabricating the microsphere based on a micromolding technique utilizing surface tension-induced droplet formation followed by photo-induced polymerization.

11 Claims, No Drawings

FABRICATION OF MACROPOROUS MONODISPERSE HYDROGEL MICROSPHERES

CROSS REFERENCE TO RELATED APPLICATIONS

This application is the National Stage of International Application No. PCT/US2016/028344, filed on Apr. 20, 2016, which claims the benefit of U.S. Application No. 62/150,626, filed on Apr. 21, 2015. The contents of both applications are hereby incorporated by reference in their entirety.

GOVERNMENT SUPPORT

This invention was made with government support under grant DMR1006613 awarded by the National Science Foundation. The government has certain rights in the invention.

BACKGROUND OF THE INVENTION

Hydrogel microparticles containing crosslinked polymer networks are capable of transporting biomolecules, e.g., proteins, through the polymeric networks. They have gained increasing attention in various biomedical applications, e.g., therapeutic agent carriers.

Desired performance of hydrogel microparticles toward specific needs can be achieved by controlling their structures such as morphology and mesh size.

Hydrogel microparticles, when fabricated via batch processes using dispersion or emulsion polymerization, are generally polydisperse, i.e., non-uniform. Microfluidics-based techniques have been utilized to fabricate highly uniform hydrogel microspheres. Yet, this approach requires complex devices and is not scalable.

Sequential layer deposition, while allowing for fabrication of multilayered hydrogel microspheres, is an arduous multiple-step procedure.

Various porogens have been used to fabricate hydrogel microparticles. However, using then often leads to non-uniform network structures and compromised mechanical integrity.

There is a need to develop facile fabrication of desirable macroporous hydrogel microspheres.

SUMMARY OF THE INVENTION

The present invention relates to a process of preparing polymeric hydrogel microspheres containing macropores. The process allows for unexpectedly facile fabrication of monodisperse (i.e., uniform) hydrogel microspheres with controlled macroporous structures. Further, the hydrogel microspheres thusly prepared exhibit an unexpectedly high protein conjugation capacity.

In one aspect, this invention is a method of fabricating a polymeric hydrogel microsphere. The method includes steps of: (1) mixing poly(ethylene glycol) diacrylate (PEGDA) and chitosan in water to form an aqueous pre-polymer solution, (2) filling an elastomeric micromold with the aqueous pre-polymer solution, (3) adding a hydrophobic wetting fluid onto the filled micromold, (4) inducing formation of a pre-polymer droplet via surface tension for 85-120 seconds, (5) exposing the pre-polymer droplet to UV light for 180-1800 seconds to crosslink the pre-polymer solution, and (6) collecting the thus-formed microsphere.

These steps are performed in series. Steps (1)-(3) are preferably conducted in a humid chamber with humidity of 90-98% (e.g., 94%).

In one embodiment, the aqueous pre-polymer solution is formed of PEGDA in a content of 5-70% v/v, preferably, 10-50% v/v, and even more preferably, 10-30% v/v.

The elastomeric micromold used in step (2) can be formed of any silicone or fluorocarbon materials. It has various geometries, e.g., cross-shaped, triangle, square, circle, pentagon, or hexagon, and also has various sizes, e.g., 1-10 nL. An example is a cross-shaped poly-dimethylsiloxane (PDMS) micromold having a size of 1.2 nL or 5.14 nL.

The hydrophobic wetting fluid used in step (3) contains a photo-initiator, e.g., 2-hydroxy-2-methylpropiophenone. A hydrocarbon solvent, e.g., n-hexadecane, can be used to prepare the hydrophobic wetting fluid.

The method of this invention can further include a step of sequentially washing the collected microsphere with 2-propanol, de-ionized water, and a saline sodium citrate buffer solution.

Another aspect of this invention is a macroporous polymeric hydrogel microsphere that can be prepared by the above-described method.

The macroporous polymeric hydrogel microsphere, containing poly(ethylene glycol) (PEG), chitosan, and water, has a diameter of 50-250 μm and a mesh size of 5-100 nm. Preferably, it has a diameter of 100-235 μm, and more preferably, 200-220 μm (e.g., 214 μm). Preferred and more preferred mesh sizes are 6-80 nm and 10-55 nm, respectively.

One embodiment of the hydrogel microsphere has a volumetric swelling ratio ($\gamma$) of 2-20 (e.g., 7.4), in which the ratio $\gamma$ is computed according to the formula:

$$\gamma = V_{wet}/V_{dry},$$

$V_{wet}$ and $V_{dry}$ being microsphere volumes under wet and dry states, respectively.

Another embodiment of the hydrogel microsphere has a water content of 40-95% v/v computed according to the following formula:

$$\text{water content} = \frac{V_{wet} - V_{dry}}{V_{wet}} \times 100\%.$$

The hydrogel microsphere, preferably, has a water content of 50-90% v/v and, even more preferably, has a water content of 65-80% v/v.

Still another embodiment of the hydrogel microsphere contains a core having a diameter of 150-190 μm (e.g., 153 or 188 μm) and a shell having a thickness of 10-30 μm (e.g., 13 or 28 μm). Note that the core, surrounded by the shell, contains more PEG and chitosan than the shell.

Chitosan is known to contain primary amines having a pKa value of 6.0-6.9 (e.g., 6.4). The chitosan in the microsphere preferably has an average molar mass of 4,500-5,500 Da (e.g., 5000 Da).

A further embodiment of the hydrogel microsphere has an apparent chitosan incorporation ratio of 0.1-1.0. The apparent chitosan incorporation ratio is calculated by normalization with the total fluorescence intensity of a hydrogel microsphere formed of 50% v/v PEGDA. For example, the hydrogel microsphere formed of 20% v/v PEGDA has a total fluorescence intensity of $3.4 \times 10^6$ AU and the microsphere formed of 50% v/v PEGDA has a total fluorescence intensity of $7.1 \times 10^6$ AU, and, as such, the hydrogel microsphere formed of 20% v/v PEGDA has an apparent chitosan incorporation ratio of 0.48 (i.e., $3.4 \times 10^6$ AU/$7.1 \times 10^6$ AU). Preferably, the hydrogel microsphere has an apparent chitosan incorporation ratio of 0.1-0.5.

As pointed out above, the chitosan in the hydrogel microsphere contains primary amines capable of conjugating with biomolecules via substitution nucleophilic $S_N2$ reaction. One embodiment of the hydrogel microsphere has $3 \times 10^{-12}$–$6 \times 10^{-11}$ moles (e.g., $3.24 \times 10^{-12}$ moles) of primary amine groups.

The details of the invention are set forth in the description below. Other features, objects, and advantages of the invention will be apparent from the following detailed description of several embodiments, and also from the appending claims.

DETAILED DESCRIPTION

Within this invention is a method of preparing macroporous monodisperse polymeric hydrogel microspheres based on a micromolding technique utilizing surface tension-induced droplet formation followed by photo-induced polymerization.

Described below is the micromolding technique used in the method of this invention for fabricating a macroporous hydrogel microsphere.

A poly-dimethylsiloxane (PDMS) micromold is prepared via thermal curing of elastomer on a photolithographically patterned silicon master mold, e.g., a PDMS micromold consists of cross-shaped microwells each having a volume of 1-10 nL.

An aqueous pre-polymer solution, which contains chitosan, poly(ethylene glycol) diacrylate (PEGDA), and de-ionized (DI) water, is prepared. Also prepared is a hydrophobic wetting fluid, e.g., a hydrocarbon solvent (such as n-hexadecane) containing a photo-initiator (such as 2-hydroxy-2-methylpropiophenone).

The pre-polymer solution is filled into each of the microwells by rubbing the micromold with a disposable pipet tip. The wetting fluid is then added onto the filled micromold at the center position of the microwell. This procedure is preferably conducted at a relative humidity of 90-98% in a humidity chamber to avoid rapid evaporation of water in the pre-polymer solution.

The filled micromold covered with the wetting fluid is left on an aluminum mirror for a specified time, e.g., 85-120 seconds, to form a pre-polymer droplet, which is generated via surface tension at the interface between the pre-polymer solution and the wetting fluid. More specifically, once the wetting fluid is applied, a pressure driving force forms along the edge of the microwell and the wetting fluid moves downward and eventually arrives at the vertices of the bottom of the microwell, thereby producing a pre-polymer droplet.

The pre-polymer droplet thus formed is exposed to UV light for a specified time, e.g., 180-1800 seconds, to polymerize, i.e. crosslink, the pre-polymer droplet. The photo-induced polymerization of PEGDA produces a crosslinked droplet that contains PEG and chitosan. The crosslinked droplet, i.e., a chitosan-PEG hydrogel microsphere, can be readily collected by pipetting and then washed with 2-propanol, DI water, and a saline sodium citrate buffer solution.

This method allows consistent and scalable fabrication of monodisperse hydrogel microspheres with mechanical integrity for a wide range of PEGDA contents.

One embodiment of the chitosan-PEG microsphere is formed of an aqueous pre-polymer solution containing short-chain chitosan (average molar mass $M_n$ 5000 Da) in a content of 0.5% w/v and PEGDA ($M_n$ 700 Da) in a content of 5-70% v/v. The chitosan-PEG microsphere is formed of PEGDA, preferably, in a content of 10-50% v/v, and more preferably, in a content of 10-30% v/v.

Morphology of the microspheres (i.e. uniform or core-shell) thus produced is controlled via polymerization-induced phase separation occurring within a specific PEGDA content range (i.e., 15-30% v/v), without any delicate controls, complex devices, or arduous multiple-step procedure.

Of note, no porogens are necessary in this method to fabricate a macroporous hydrogel microsphere.

Also within this invention is a macroporous hydrogel microsphere prepared by the method described above. The chitosan-PEG hydrogel microsphere has a diameter of 50-250 µm and a mesh size of 5-100 nm, depending on the PEGDA content of the aqueous pre-polymer solution from which the microsphere is formed.

The PEGDA content also contributes to the swelling ratio and the water content of the chitosan-PEG hydrogel microsphere. Microspheres in two different states, i.e., wet (or swollen) state and dry (or shrunken) state, are prepared. The wet state is reached by soaking the microsphere in a 5× saline sodium citrate buffer solution for one day and the dry state is reached by drying the microsphere in a vacuum chamber for one day. Throughout the entire range of the PEGDA content, wet (i.e., swollen state) microspheres have minimal differences in diameter (less than 15%). By contrast, the diameters of dry (i.e., shrunken state) microspheres decrease significantly with decreasing PEGDA contents. The difference in diameter between wet and dry states is greater when the PEGDA content is lower and, as such, the volumetric swelling ratio ($\gamma$) between microspheres formed of a 10% v/v PEGDA solution ($\gamma=7.4$) is greater than that between microspheres formed of a 50% v/v PEGDA solution ($\gamma=2.0$). Accordingly, the water content of a wet microsphere can be as high as 87% when the PEGDA content is as low as 10% v/v. Additionally, confocal microscopy indicates highly uniform, i.e., monodisperse, microspheres for all PEGDA contents. Importantly, a microsphere formed of a solution having a PEGDA content as low as 5% v/v also retains uniform spherical shape, as well as mechanical integrity determined by an unconfined compression assay.

Two different phases, i.e., core and shell, in the microspheres are formed only at 15-30% v/v PEGDA contents, indicating that the polymerization-induced core-shell phase separation occurs within a specific PEGDA content range. The core contains higher contents of both PEG and chitosan than the shell. In one example, the hydrogel microsphere formed of a 20% v/v PEGDA solution contains a core having a diameter of 153 µm and a shell having a thickness of 28 µm. In another example, the hydrogel microsphere formed of a 30% v/v PEGDA solution contains a core having a diameter of 188 µm and a shell having a thickness of 13 µm.

Fluorescently labeled microspheres analyzed by confocal microscopy (see EXAMPLE 3 below for details) show distinguishable fluorescence intensities on the microspheres formed of various PEGDA contents. In one study, distribution of chitosan in the microspheres was confirmed via a substitution nucleophilic $S_N2$ reaction of primary amines in chitosan with carboxyfluorescein succinimidyl ester. In another study, PEG distribution was confirmed via non-covalent hydrophobic absorption of a red fluorescent dye sulforhodamine B. In such studies, total fluorescence intensity is an indicator of both the chitosan incorporation and the PEG distribution in a microsphere. In detail, the 10% v/v PEGDA microsphere shows weak yet uniform fluorescence (fluorescence intensity or FI=41±9). The 20% v/v and 30% v/v PEGDA microspheres show lower fluorescence at the shell of the microspheres (FI=50±3 and 85±2 for 20% v/v and 30% v/v PEGDA, respectively) than around the core (FI=240±6 and 189±5 for 20% v/v and 30% v/v PEGDA, respectively), indicating relatively lower chitosan incorporation in the shells. These chitosan-rich cores and the chitosan-poor shells correspond well with the PEG-rich cores and the PEG-poor shells at 20% v/v and 30% v/v PEGDA contents, respectively. The chitosan-rich core expands with increasing PEGDA contents and occupies most of the microsphere formed of a 40% v/v PEGDA solution. The 70% v/v PEGDA microspheres shows irregular fluorescence regions, indicating aggregated chitosan.

The microsphere fabricated with long-chain chitosan (molecular weight MW~200 kDa) shows fluorescence intensity (also see EXAMPLE 3 below for details) equivalent to that with short-chain chitosan (average molar mass $M_n$ 5 kDa), indicating that major portions of the short-chain chitosan are incorporated with retained chemical reactivity of its primary amines. The primary amines in chitosan having a pKa value of 6.0-6.9 (e.g., about 6.4) can be readily enlisted for covalent conjugation with biomolecules, modified or unmodified, via substitution nucleophilic $S_N2$ reaction with reactive groups in the biomolecules (e.g., isothiocyanates, N-hydroxysuccinimide esters, or sulfonyl chlorides) under neutral pH conditions. Note that the pKa values of common amine-containing components, unlike the primary amines in chitosan, are above 9 (e.g., 10.5 for lysine, ≥9 for N-terminal groups of amino acids, and 9-10 for aminosilane), making them heavily protonated and much less efficient for amine-reactive reactions under neutral pH conditions.

The polymerization of PEGDA to form PEG induces phase separation to form a core and a shell in the microsphere, which in turn contributes to the distribution of chitosan due to its migration and thus the corresponding chitosan incorporation ratio. Copolymerization of acrylate-modified chitosan with PEGDA has been confirmed to suppress the mobility of chitosan.

In one example, alkyne-azide cycloaddition reactions are performed to evaluate conjugation (see EXAMPLE 3 below for details) to chitosan-PEG microspheres of two biomolecules, i.e., fluorescein-labeled single-stranded DNA (F-ssDNA, MW 6 kDa) and red fluorescent protein R-phycoerythrin (R-PE, MW 240 kDa). The fluorescence micrographs demonstrate that the microsphere fabricated with a 10% v/v PEGDA solution shows uniform fluorescence throughout the microsphere for both F-ssDNA and R-PE, while the microsphere fabricated with 20-30% v/v PEGDA shows higher fluorescence near the surface.

The results set forth above indicate that the mesh size of the microsphere formed of 10% v/v PEGDA is large enough for both biomolecules (i.e. F-ssDNA, radius of gyration $R_g \approx 2$ nm and R-PE, hydrodynamic radius $R_h \approx 5.6$ nm) to penetrate into the microsphere. In other words, most of the primary amine groups of chitosan in the microsphere are readily accessible, leading to high capacity for conjugation of both F-ssDNA and R-PE.

On the other hand, both biomolecules penetrate and are conjugated only in the shell of the microspheres formed of a 20% v/v or 30% v/v PEGDA solution.

Another study has confirmed that the mesh sizes of the 10% v/v and 20% v/v PEGDA microspheres are not large enough for the penetration of a substantially larger supramolecule, i.e. nanotubular tobacco mosaic virus (TMV, 18×300 nm dimension and $R_h \approx 55$ nm).

The results described above indicate that the mesh sizes of the microspheres, when formed of 10% v/v to 30% v/v PEGDA solutions, are uniform throughout the macroporous regions, substantially larger than R-PE ($R_h \approx 5.6$ nm) yet smaller than TMV ($R_h \approx 55$ nm).

The number of primary amines (i.e., conjugation sites) in a microsphere can be readily calculated.

For example, the number of incorporated chitosans in a 10% v/v PEGDA microsphere is computed according to the formula:

$$N_{CS} = V_M \times C_{CS} \times \eta \times \frac{1}{MW_{CS}} =$$
$$1.20 \text{ nL} \times \frac{0.5 \text{ g}}{100 \text{ mL}} \times 0.1 \times \frac{\text{moles}}{5000 \text{ g}} = 1.20 \times 10^{-13} \text{ moles},$$

wherein $V_M$ represents droplet volume (equivalent to the micromold volume $V_M$=1.20 nL), $C_{CS}$ represents chitosan content (0.5% w/v), η represents apparent chitosan incorporation ratio (η=0.1; see discussions above), and $MW_{CS}$ represents molecular weight of chitosan (5000 Da).

The number of the primary amines per chitosan with 90% deacetylation is:

$$n_{Am} = \frac{MW_{CS}}{MW_{R-CS}} \times 0.9 = \frac{5000}{161} \approx 27,$$

wherein $MW_{R-CS}$ represents molecular weight of the glucosamine repeating unit of the chitosan, i.e., 161 Da.

Thus, the microsphere containing chitosan can have the number of the primary amines (i.e. conjugation sites) of $$N_{Am} = N_{CS} \times n_{Am} = 3.24 \times 10^{-12} \text{ moles}.$$

As set forth above, the macroporous hydrogel microsphere prepared using the method of this invention is capable of transporting biomolecules conjugated to it. The microsphere can be used in various biomedical applications including, among others, therapeutic agent carriers, biosensing platforms, and building blocks for tissue engineering.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publication cited herein is incorporated by reference.

Example 1

Fabrication of a Chitosan-PEG Hydrogel Microsphere

A chitosan-PEG hydrogel microsphere was fabricated via a micromolding-based approach following the procedure described below.

A poly-dimethylsiloxane (PDMS) micromold was prepared via thermal curing (overnight at 65° C.) of Sylgard 184 elastomer (9:1 weight ratio of elastomer to curing agent) on a photolithographically patterned silicon master mold. The PDMS micromold consists of cross-shaped microwell with 1.20 nL or 5.14 nL of volume.

An aqueous pre-polymer solution was prepared by mixing chitosan (0.5% w/v), poly(ethylene glycol) diacrylate (PEGDA) (5-70% v/v) and de-ionized (DI) water, and a hydrophobic wetting fluid was prepared by mixing n-hexadecane and 2-hydroxy-2-methylpropiophenone (photoinitiator or PI, 1% v/v). The pre-polymer solution was filled into the microwell by rubbing the micromold with a disposable pipet tip. The wetting fluid was then added onto and covered the filled micromold. These procedures were conducted in a humidity chamber with humidity of about 94% to avoid rapid evaporation of water in the pre-polymer solution. The micromold covered with the wetting fluid was left on an aluminum mirror (Thorlabs, Newton, N.J.) for about 120 seconds to form a pre-polymer droplet via surface tension at the interface between the pre-polymer solution and the wetting fluid. The pre-polymer droplet thus formed was exposed to 365-nm UV light with an 8-W hand-held UV lamp (Spectronics Corp., Westbury, N.Y.) for 180 seconds to polymerize the pre-polymer droplet (i.e. crosslinking). The crosslinked droplet, i.e., a chitosan-PEG hydrogel microsphere, was collected by pipetting and then washed 5 times with 2-propanol, 3 times with DI water containing 0.5% (v/v) TW20, and 2 times with 5× saline sodium citrate (SSC) buffer solution containing 0.05% (v/v) TW20 (SSC-TW20 buffer solution).

A hydrogel microsphere formed of a 10% v/v PEGDA solution in a 1.20 nL-PDMS micromold had a diameter of 132 μm, compared with a diameter of 207 μm of a microsphere formed in a 5.14 nL-PDMS micromold.

Example 2

Evaluation of the Swelling Ratio and Water Content of a Chitosan-PEG Hydrogel Microsphere A study was performed to evaluate the swelling ratio and water content of a chitosan-PEG hydrogel microsphere following the procedure described below.

A chitosan-PEG microsphere formed of 10% v/v PEGDA was immersed in a SSC-TW20 buffer solution for at least 1 day to reach equilibrium swelling (i.e. wet state). The microsphere was then dried in a vacuum chamber at room temperature for at least 1 day upon washing 5 times with deionized water. The microsphere was imaged under a bright-field mode, and the microsphere diameter was determined with image analysis software ImageJ (Rasband, W. S. Imagej; U. S. National Institutes of Health: Bethesda, Md., 1997-2012) in order to compute the volumetric swelling ratio (γ):

$$\gamma = V_{wet}/V_{dry},$$

and the water content:

$$\text{water content} = \frac{V_{wet} - V_{dry}}{V_{wet}} \times 100\%,$$

$V_{wet}$ and $V_{dry}$ being microsphere volumes under wet and dry states, respectively.

The microsphere was found to have a volumetric swelling ratio of 7.4 and a water content of 87%.

Example 3

Evaluation of the 3D Network Structure and Biomolecular Conjugation of a Chitosan-PEG Hydrogel Microsphere A study was performed to evaluate both the 3D network structure and the biomolecular conjugation of a chitosan-PEG hydrogel microsphere following the procedure described below.

To fluorescently label a chitosan-PEG hydrogel microsphere, the hydrogel microsphere was incubated in a SSC-TW20 buffer solution with 5 μM of 5-(and 6-) carboxyfluorescein N-hydroxysuccinimide ester (NHS-fluorescein, Pierce Biotechnology, Ill.) for 1 hour at room temperature. Unreacted fluorescein residues were removed by washing the microsphere 3 times with an aqueous solution containing 2-propanol (50% v/v). A fluorescently labeled chitosan-PEG hydrogel microsphere was thus obtained.

A red fluorescent protein R-phycoerythrin (R-PE) buffer solution was exchanged for a borate buffered saline buffer solution (50 mM borate, 300 mM NaCl, pH 8.5) via centrifugal filtration at 4° C. The resulting R-PE solution (2 mg/mL) was then reacted with 20-fold molar excess of Trans-cyclooctene (TCO)-$PEG_4$-N-hydroxysuccinimide (NHS) ester (Click Chemistry Tools, Scottsdale, Ariz.) or NHS-$PEG_{12}$-azide (Thermo Fisher Scientific, Waltham, Mass.) for 30 minutes at room temperature. Unreacted chemicals were separated from the R-PE solution via centrifugal filtration (Amicon Ultra 0.5) with phosphate buffered saline buffer solution (pH 7.4). The azide-activated R-PE was thus formed.

The fluorescently labeled chitosan-PEG hydrogel microsphere was activated upon incubation with 500 μM of azadibenzocyclooctyne (ADIBO)-sulfo-NHS ester (Click Chemistry Tools, Scottsdale, Ariz.) in a SSC-TW20 buffer solution (20× concentrate, molecular biology grade, Sigma-Aldrich) for 1 hour at room temperature. Unreacted chemicals were removed by washing the microsphere 4 times with the SSC-TW20 buffer solution.

To examine the 3D network structure and protein conjugation capacity of the hydrogel microsphere, the ADIBO-activated microsphere was reacted with 2 μM of the azide-activated R-PE for 24 hours in the SSC-TW20 buffer solution at room temperature. Unconjugated biomolecules were separated from the microsphere solution by washing the microsphere 5 times with the SSC-TW20 buffer solution.

The fluorescently labeled R-PE conjugated microsphere thus obtained was imaged with an epifluorescence microscope (Olympus BX51 equipped with a DP70 microscope digital camera, Center Valley, Pa.) and a confocal microscope (Leica DMIRE2 equipped with a TCS SP2 scanner, Wetzlar, Germany) in the SSC-TW20 buffer solution (pH 7.0). Epifluorescence micrographs of the microsphere were obtained with a 10× objective under standard green (U-N31001) and red (U-N31002) filter set (Chroma Technology Corp., Rockingham, Vt.) for the green fluorescent molecule (fluorescein) and the R-PE, respectively. Confocal micrographs of the microsphere were obtained with a 20× objective at 488 nm and 543 nm excitation for the green fluorescent molecule and the R-PE, respectively. Diameters and fluorescence intensities of the microsphere were determined with the image analysis software ImageJ.

It was found that the 10% v/v PEGDA microsphere with a diameter 132 μm had a total fluorescence intensity of about $90 \times 10^6$ AU, compared with about $300 \times 10^6$ AU for that having a diameter of 207 μm. In other words, the conjugation capacity of the larger microsphere (207 μm) is about 3.5 times that of the smaller one (132 μm).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A polymeric hydrogel microsphere, comprising a core, a shell, wherein the core comprises crosslinked-poly(ethylene glycol) (PEG), chitosan, and water; wherein the microsphere has a diameter of 50-250 μm and a mesh size of 5-100 nm; the core has a diameter of 150-190 μm; the shell has a thickness of 10-30 μm; and the core is surrounded by the shell.

2. The polymeric hydrogel microsphere of claim 1, wherein the microsphere has a volumetric swelling ratio of 2-20 and a water content of 40-95% v/v.

3. The polymeric hydrogel microsphere of claim 2, wherein the microsphere has a diameter of 100-235 μm and a water content of 50-90% v/v.

4. The polymeric hydrogel microsphere of claim 3, wherein the microsphere has a diameter of 200-220 μm and a water content of 65-80% v/v.

5. The polymeric hydrogel microsphere of claim 1, wherein the microsphere has a diameter of 200-220 μm and a water content of 65-80% v/v.

6. The polymeric hydrogel microsphere of claim 1, wherein the chitosan has an average molar mass of 4,500-5,500 Da.

7. The polymeric hydrogel microsphere of claim 6, wherein the chitosan comprises primary amines each having a pKa value of 6.0-6.9.

8. The polymeric hydrogel microsphere of claim 6, wherein the microsphere has an apparent chitosan incorporation ratio of 0.1-1.0.

9. The polymeric hydrogel microsphere of claim 8, wherein the microsphere has a diameter of 200-220 μm and a water content of 65-80% v/v.

10. The polymeric hydrogel microsphere of claim 1, wherein the microsphere has a diameter of 200-220 μm, a water content of 75-90% v/v, and an apparent chitosan incorporation ratio of 0.1-0.5.

11. The polymeric hydrogel microsphere of claim 10, wherein the microsphere has $3 \times 10^{-12}$-$6 \times 10^{-11}$ moles of primary amine groups.

* * * * *